(12) United States Patent
Sobelman et al.

(10) Patent No.: US 10,016,294 B2
(45) Date of Patent: *Jul. 10, 2018

(54) METHOD OF IMPLANTING AN INTRAGASTRIC BALLOON

(71) Applicant: Apollo Endosurgery, Inc., Austin, TX (US)

(72) Inventors: Owen Shawn Sobelman, Shingle Springs, CA (US); Janel A. Birk, Oxnard, CA (US)

(73) Assignee: APOLLO ENDOSURGERY US, INC., Austin, TX (US)

( * ) Notice: Subject to any disclaimer, the term of this patent is extended or adjusted under 35 U.S.C. 154(b) by 393 days.

This patent is subject to a terminal disclaimer.

(21) Appl. No.: 14/700,092

(22) Filed: Apr. 29, 2015

(65) Prior Publication Data

US 2015/0230957 A1   Aug. 20, 2015

Related U.S. Application Data

(60) Division of application No. 13/667,617, filed on Nov. 2, 2012, now Pat. No. 9,174,033, which is a division (Continued)

(51) Int. Cl.
*A61M 29/02* (2006.01)
*A61F 5/00* (2006.01)

(52) U.S. Cl.
CPC ............ *A61F 5/003* (2013.01); *A61M 29/02* (2013.01)

(58) Field of Classification Search
CPC ........ A61B 17/12022; A61B 17/12031; A61B 17/12036; A61B 17/12136;

(Continued)

(56) References Cited

U.S. PATENT DOCUMENTS

| 563,287 A | * | 7/1896 | Lane et al. ............. A63H 27/10 |
| | | | 137/223 |
| 1,702,974 A | | 2/1929 | MacDonald |

(Continued)

FOREIGN PATENT DOCUMENTS

| DE | 8804765 U1 | 6/1989 |
| WO | 2005007231 A1 | 1/2005 |

OTHER PUBLICATIONS

Living With the Bib/BioEnterics Intragastric Balloon Program,' Inamed Health; Patient Information Brochure; p. 1.; May 1, 2005.

(Continued)

*Primary Examiner* — Darwin Erezo
*Assistant Examiner* — Katherine Schwiker
(74) *Attorney, Agent, or Firm* — Donald K. Jones (57) ABSTRACT

A method includes providing an inflatable implant formed of a flexible polymer material suitable for residence in the body. The implant includes a slit valve provided in its wall. The slit valve includes an elastomeric valve body with an open internal chamber being in fluid communication with a proximal opening of the valve, a concave section at its distal end, and a normally closed slit in a solid portion of the valve body connecting the concave section and the distal end of the valve body. An inflation tube having an injection tip with a distal end and an insertion stop is provided. The injection tip is inserted into the internal chamber of the slit valve until the insertion stop positively engages the proximal opening. Then, the implant with the inflation tube is delivered to a body cavity. Once delivered, fluid is introduced through the inflation tube and into the implant.

6 Claims, 6 Drawing Sheets

Related U.S. Application Data of application No. 12/785,710, filed on May 24, 2010, now abandoned, which is a continuation of application No. 10/561,515, filed as application No. PCT/US03/19414 on Jun. 20, 2003, now Pat. No. 7,749,254.

(58) Field of Classification Search
CPC ........ A61B 17/3462; A61B 2017/1205; A61B 17/12054; A61B 17/22051; A61B 17/22064; A61B 17/22062; A61B 1/015; A51M 2025/1054; A61M 29/02; A61M 2029/025; A61M 39/20; A61M 39/045; A61M 39/26; A61M 39/00; A61M 39/24; A61M 39/10; A61M 39/1011; A61M 39/22; A61M 39/223; A61M 39/225; A61M 39/227; A61M 39/228; A61M 2039/0009; A61M 2039/2406; A61M 2039/2413; A61M 2039/242; A61M 2039/2426; A61M 2039/2473; A61M 2039/224; A61M 2039/226; A61M 61/2406; A61M 2039/2433; A61M 2039/244; A61M 39/1072; A61M 25/1025; A61M 25/1018; A61M 25/10181; A61M 25/10182; A61M 25/10185; A61M 25/10186; A61F 5/003; A61F 5/0036; A61F 5/004; A61F 5/0043; A61F 5/0046; A61F 5/005; A61F 5/0053; A61F 5/0056; A61F 5/0089; A61F 5/0066; A61F 5/0076; A61F 5/0079; A61F 5/0013; A61F 5/0063; A61F 5/0069; A61F 6/146; A61F 6/16; Y10T 137/7886; Y10T 137/788; Y10T 137/7882; Y10T 137/3584; F16K 15/147
USPC .......... 137/223, 844, 846, 850; 606/192–195
See application file for complete search history.

(56) References Cited

U.S. PATENT DOCUMENTS

| | | | |
|---|---|---|---|
| 3,919,724 A | 11/1975 | Sanders | |
| 4,430,392 A | 2/1984 | Kelley | |
| 4,436,519 A | 3/1984 | ONeill | |
| 4,485,805 A | 12/1984 | Foster | |
| 4,607,618 A | 8/1986 | Angelchik | |
| 4,636,213 A | 1/1987 | Pakiam | |
| 4,694,827 A | 9/1987 | Weiner | |
| 4,715,360 A | 12/1987 | Akui | |
| 4,930,535 A | 6/1990 | Rinehold | |
| 5,084,061 A | 1/1992 | Gau | |
| 5,113,571 A * | 5/1992 | Manska | A61M 39/10 285/332 |
| 5,113,911 A * | 5/1992 | Hirsh | A61M 39/22 137/844 |
| 5,205,834 A | 4/1993 | Moorehead | |
| 5,211,371 A | 5/1993 | Coffee | |
| 5,242,413 A | 9/1993 | Heiliger | |
| 5,250,029 A | 10/1993 | Lin | |
| 5,251,873 A | 10/1993 | Atkinson et al. | |
| 5,269,764 A | 12/1993 | Vetter | |
| 5,513,630 A * | 5/1996 | Century | A61M 15/0028 128/203.12 |
| 5,599,327 A | 2/1997 | Sugahara | |
| 5,725,507 A | 3/1998 | Petrick | |
| 5,819,749 A | 10/1998 | Lee | |
| 5,823,852 A | 10/1998 | Chu | |
| 5,843,046 A | 12/1998 | Motisi | |
| 5,916,198 A | 6/1999 | Dillow | |
| 6,039,748 A | 3/2000 | Savage | |
| 6,102,897 A | 8/2000 | Lang | |
| 6,261,268 B1 | 7/2001 | Mayer | |
| 6,322,572 B1 | 11/2001 | Lee | |
| 6,364,867 B2 | 4/2002 | Wise | |
| 6,419,699 B1 | 7/2002 | Schuessler | |
| 6,439,541 B1 | 8/2002 | Noesel | |
| 6,454,785 B2 | 9/2002 | DeHoyosGarza | |
| 6,503,264 B1 | 1/2003 | Birk | |
| 6,579,301 B1 | 6/2003 | Bales | |
| 6,629,776 B2 | 10/2003 | Bell | |
| 6,733,512 B2 | 5/2004 | McGhan | |
| 6,733,513 B2 | 5/2004 | Boyle | |
| 6,746,460 B2 | 6/2004 | Gannoe | |
| 6,840,257 B2 | 1/2005 | Dario | |
| 7,020,531 B1 | 3/2006 | Colliou | |
| 7,037,344 B2 | 5/2006 | Kagan | |
| 7,056,305 B2 | 6/2006 | GarzaAlvarez | |
| 7,214,233 B2 | 5/2007 | Gannoe | |
| 2002/0055757 A1 * | 5/2002 | Torre | A61B 17/12099 606/192 |
| 2002/0082546 A1 | 6/2002 | Crank | |
| 2004/0254625 A1 * | 12/2004 | Stephens | A61B 17/12022 623/1.1 |
| 2005/0055039 A1 | 3/2005 | Burnett | |
| 2005/0192615 A1 | 9/2005 | Torre | |
| 2005/0240279 A1 | 10/2005 | Kagan | |
| 2005/0267595 A1 | 12/2005 | Chen | |
| 2005/0267596 A1 | 12/2005 | Chen | |
| 2006/0142700 A1 | 6/2006 | Sobelman | |
| 2007/0016262 A1 | 1/2007 | Gross | |
| 2007/0083224 A1 | 4/2007 | Hively | |
| 2007/0156248 A1 | 7/2007 | Marco | |

OTHER PUBLICATIONS

BIB Bioenterics Intragastric Balloon Program, Take Control of Your Weight and Your Life/The Solution for You, Inamed Health, pp. 1-2; Jan. 19, 2004.
BIB Bioenterics Intragastric Balloon Program, Taking the Next Step/Take Control of Your Weight and Your Life, Inamed Health, pp. 1-9; Apr. 29, 2004.
BIB Data Sheet Directions for Use, 'BioEnterics Intragastric Balloon System,' Inamed Health, 1-12 pp.; Rev 03, 2105.

* cited by examiner

METHOD OF IMPLANTING AN INTRAGASTRIC BALLOON

CROSS-REFERENCE TO RELATED APPLICATION

This application is a divisional of U.S. patent application Ser. No. 13/667,617, filed Nov. 2, 2012, which is a divisional of U.S. patent application Ser. No. 12/785,710, filed May 24, 2010, now abandoned, which is a continuation of U.S. patent application Ser. No. 10/561,515, filed Dec. 20, 2005, now U.S. Pat. No. 7,749,254, which is a national stage application under 35 U.S.C. § 371 of PCT Patent Application No. PCT/US2003/019414, filed Jun. 20, 2003, each of which is incorporated herein by reference in its entirety.

BACKGROUND OF THE INVENTION

Field of the Invention

The present invention is directed to a slit valve that enables two-way fluid flow, and in particular a slit valve for use with implantable, inflatable medical devices such as gastric balloons for the treatment of obesity.

Description of the Related Art

There are a wide variety of known inflatable devices that can be implanted in the body. One such inflatable implantable medical device is a gastric balloon, as described in U.S. Pat. No. 5,084,061, or commercially available as the Bio-Enterics Intragastric Balloon System (sold under the trademark BIB®). These devices are designed to provide therapy for moderately obese individuals who need to shed pounds in preparation for surgery, or as part of a dietary or behavioral modification program.

The BIB System, for example, consists of a silicone elastomer gastric balloon that is inserted into the stomach and filled with fluid. Commercially available gastric balloons are filled with saline solution or air. The gastric balloon functions by filling the stomach and enhancing appetite control. Placement of the gastric balloon is non-surgical, usually requiring no more than 20-30 minutes. The procedure is performed endoscopically in an outpatient setting, using local anesthesia and sedation. Placement is temporary, and gastric balloons are typically removed after six to twelve months.

Figure 1:
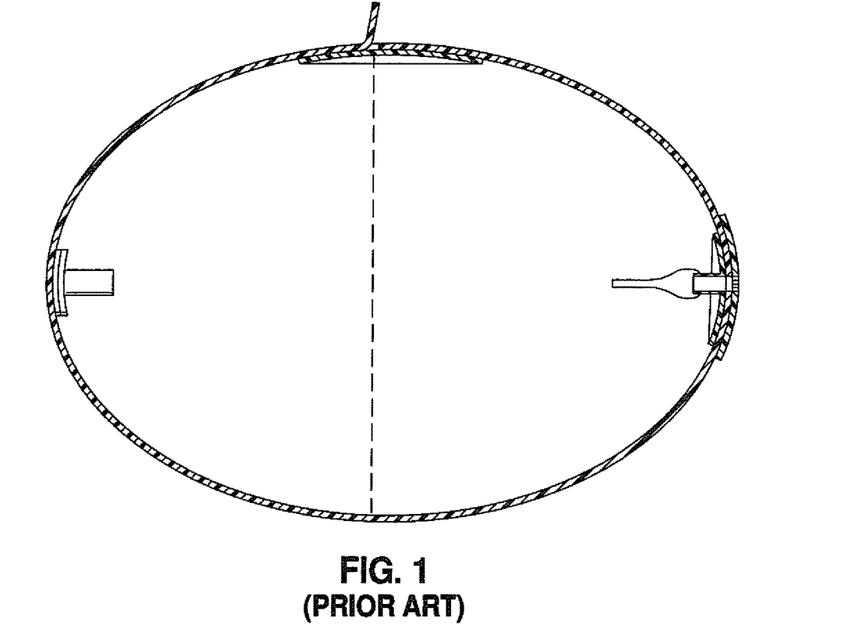
FIG. 1 is a cross sectional view of a prior art gastric balloon with a one-way valve.

There are known in the prior art a variety of valves for use with such gastric balloons. For example, the valve described in U.S. Pat. No. 5,084,061, shown in FIG. 1, consists essentially of a leaf valve (also known as a duckbill valve) comprising two relatively flat pieces of silicone elastomer bonded along their longitudinal edges and affixed by adhesive to the end of the valve stem. In operation, a filler tube, which is usually a plastic or silicone tube containing a stainless steel stiffening rod, is inserted through an X-shaped slot, through a hole, through a tubular valve stem, through a second X-shaped slot in the membrane, and through the leaf valve until the filler tube itself is in the interior of the shell. In such a position, both addition and withdrawal of fluid can be accomplished. For addition of fluid only, the filler tube does not need to penetrate through the leaf valve.

However, valves of this sort have several disadvantages. Initially, these valves are prone to leaking one way in which a duckbill valve may develop leaks is through the initial filling of the balloon when one of the flat pieces of elastomer becomes kinked or develops a curvature through which the fluid can pass. Another way is through the fluid removal process, which requires the insertion of the filler tube completely through the valve and into the interior of the shell. Following removal of a portion of the fluid and the filler tube, the leaf valve can remain partially open. This causes even greater amounts of the fluid to be released from the implant. Accordingly, there is a need for a valve that does not leak following either filling or removal of fluid from the shell.

Second, the prior art leaf valves face opposing problems in that it is necessary to reduce the pressure necessary to insert the filler tube into the valve to ease in installation and filling, but if there is not a sufficiently tight fit between the filler tube and the valve, then the pressure of the fluid in the balloon or valve may force the filler tip out of the valve before filing is complete. Further, it is necessary to consider the amount of force necessary to remove the fill tube from the valve. Current designs, such as that discussed above, often require too much pressure to insert the filler tube into the valve and too much pressure to remove the filler tube from the valve. Alternatively, in instances where the pressure necessary to insert and remove the filler tube are not great, the filler tube may pop out of the valve while filling the balloon. Accordingly, there is a need for a valve that promotes easy insertion and removal of the filler tube, but does not force the filler tube out of the valve while filling the balloon. Prior art leaf valves are also unsuitable at fluid inflation pressures above 30 psi, which may damage the valve.

Finally, the prior art duckbill valves have the shortcoming that they are only one-way valves. They cannot be used to direct fluid flow in both directions without inserting a tube completely through the valve. Situations arise where it is preferable to have a two-way valve. For example, when a device absorbs additional fluid through osmosis after being implanted in the body and filled to a proper volume, it may be desirable to reduce the fluid volume of that implant. In the duckbill valve described above, no amount of pressure on the interior of the balloon will permit egress of the fluid contained therein. Accordingly, there is a need to a valve that is capable, of permitting back flow of fluid (i.e., from the interior to the exterior), while generally preventing egress of fluid when under normal pressure.

Another type of valve often used in implant technology is a diaphragm valve, such as a that discussed in U.S. Pat. No. 6,419,699 assigned to McGhan Medical Corporation. The diaphragm valve requires insertion of a rigid male component on the inflation tube to open the valve and allow fluid transfer. Upon removal of the inflation tube, fluid pressure within the implant forces the valve closed and creates a leak proof seal. As with the leaf valve, such a valve does teach any means for backflow through the valve.

Other valves that are used in medical applications include a connector for an instrument insertion passage described in U.S. Pat. No. 5,599,327 ("the '327 patent"), a non-binding surgical valve as described in U.S. Pat. No. 5,916,198 ("the '198 patent"), and a needle less injection site as described in U.S. Pat. No. 6,261,268 ("the '268 patent"). Each of these valves or connectors has shortcomings that are addressed by the present invention. Initially, both the '327 and the '268 patents contemplate an opening in the valve that forms a seal with the application of mechanical pressure by a medical instrument. Accordingly, both the '327 and '268 patents require the use of bulky components and mechanical force to create a seal. Such components and use of mechanical force are not conducive for use with implant technology. Further, the '198 patent describes a one-way valve that is closed by insufflation gases acting on an interior surface of the valve via a passage in one of the valve segments. Accordingly, the valve contemplated by the '198 patent does not overcome the shortcomings of the prior art discussed above. Therefore, the present invention is directed at overcoming these problems associated with the prior art valves. The present invention is related to a two-way valve that is usable in an implantable medical device such as a gastric balloon. These and other characteristics of the present invention will become apparent from the further disclosure to be made in the detailed description given below.

SUMMARY OF THE INVENTION

The present invention is directed to a two-way valve having first and second ends. The two-way valve includes a substantially cylindrical valve body having a slit connecting the first and second ends of the valve and concave sections formed in the first and second ends.

The present invention is further directed to a slit valve having a flange surface with an opening therein. The slit valve has a valve body connected to the flange surface and a chamber formed in the valve body for accepting an inflation tube inserted through the opening in the flange surface. The slit valve has a concave section at one or both ends, which are connected by a slit formed in the valve body.

The present invention is also directed to an implantable, inflatable apparatus having a slit valve. The slit valve includes a flange surface having an opening. The slit valve also includes a valve body connected to the flange surface, a first chamber formed in the valve body for accepting an inflation tube inserted through the opening in the flange surface, a concave section located at one or both ends of the valve, and a slit formed in the valve body connecting the two ends.

The present invention is also directed to a medical apparatus for the treatment of obesity. The medical apparatus includes a balloon formed of a suitable polymer or elastomer material for insertion into the stomach, and a slit valve for communication of a fluid from an inflation tube to the balloon. The slit valve includes a flange surface having an opening therein, a valve body connected to the flange surface, a first chamber formed in the valve body for accepting the inflation tube inserted through the opening in the flange surface, a concave section located at one or both ends of the valve, and a slit formed in the valve body connecting the two ends.

Further characteristics, features, and advantages of the present invention will be apparent upon consideration of the following detailed description of the invention take in conjunction with the following drawings, and in which:

DETAILED DESCRIPTION OF THE PREFERRED EMBODIMENTS

Figure 3:
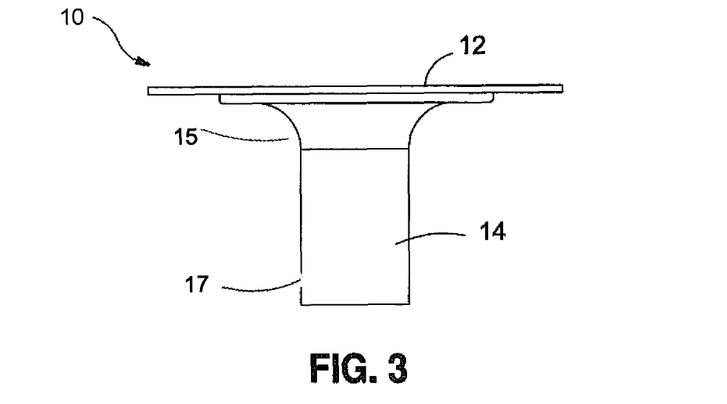
FIG. 3 is a side view of a two-way slit valve according to one of the embodiments of the present invention.

A slit valve 10 in accordance with a first embodiment of this invention is shown in FIG. 3. The valve comprises a valve body 14 and a flange 12. With respect to the description of this invention, the end of the valve 10 on which the flange 12 is located will be called the top of the valve and the opposite end the bottom. The valve 10 is preferably formed of an elastomeric material such as silicone; however, other materials may be used without departing from the scope of this invention. The valve body 14 is preferably molded in a substantially cylindrical shape. The cylindrical shape is preferred as it provides added rigidity and stiffness for the valve. The valve body 14 has a proximal end 15 and a distal end 17.

Figure 4:
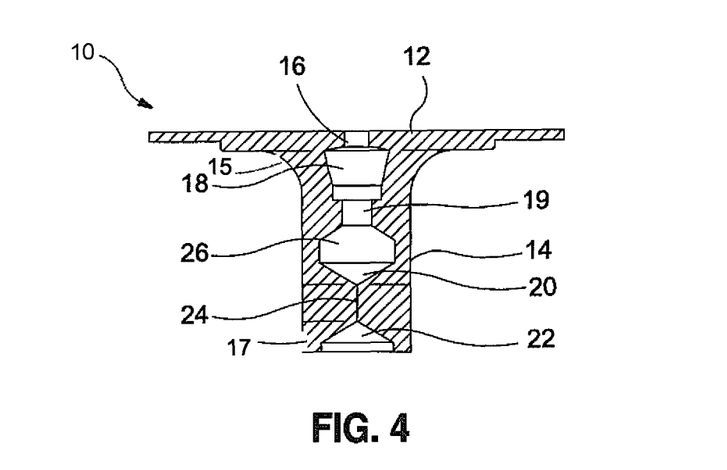
FIG. 4 is a cross-sectional view of the two-way valve shown in FIG. 3.
Figure 5:
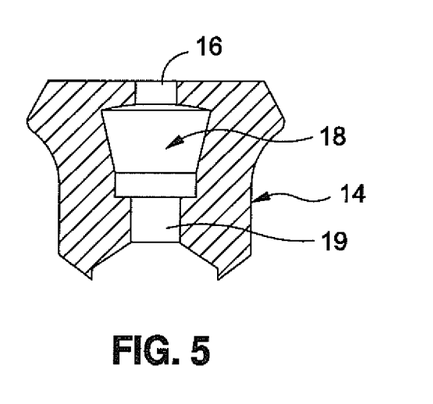
FIG. 5 is a close-up view of a portion of the two-way valve shown in FIG. 4.
Figure 6:
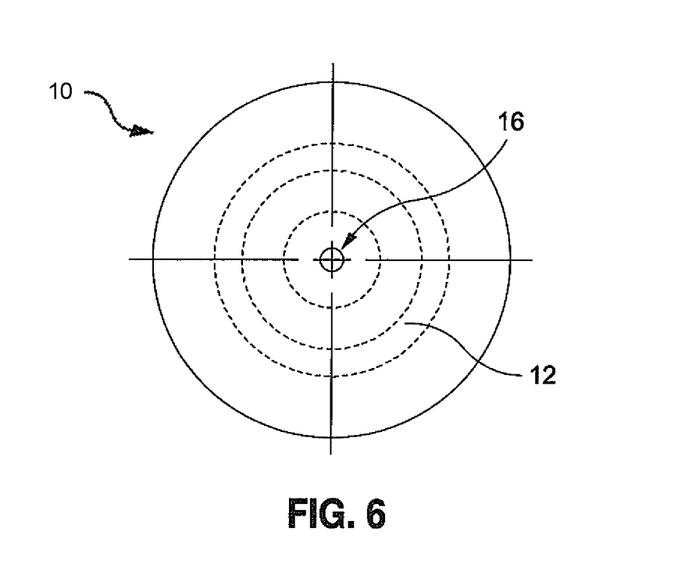
FIG. 6 is a top view of the two-way valve according to another aspect of the present invention.

FIGS. 4 and 5 show cross-sectional views of the valve 10. FIG. 6 shows a top view of valve 10. Starting at the flange surface 12 of the top of the valve 10, there is an opening 16 through the flange 12 that is in communication with interior surfaces of the valve 10. Immediately below the opening 16 is a first chamber 18. Beneath the first chamber 18 is a neck 19. The neck 19 separates the first chamber 18 from a second chamber 26. At the bottom of the second chamber is a concave surface 20. The concave surface 20 is preferred because it provides guidance to a probe in the event that the sealing properties of valve 10 need to be overcome mechanically. The concave surface 20 assists in the guidance of a probe (not shown) that can be used to force the valve to open and allow for reverse flow of fluid contained by the valve 10.

Following the concave surface 20 is a slit 24 in a substantially solid portion of the body 14. The slit 24 connects and is in fluid communication with a second surface 22, which may be concave as shown, or flat. In an application such as a gastric balloon, fluid enters the balloon shell as it exits the bottom side of the slit 24. The slit 24 may be lubricated with silicone oil. The use of silicone oil eases the insertion of a removal tip (not shown) in instances where it is desired to overcome the sealing properties of the valve 10, and serves to reduce the chance of cross-linking where the valve body 14 is made of silicone.

Figure 7:
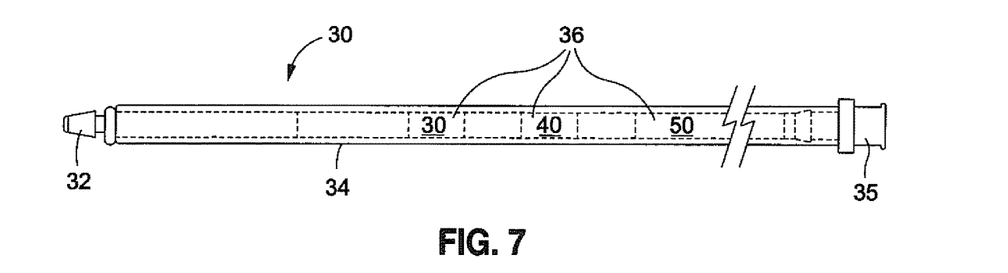
FIG. 7 is side view of a filler-tube according to another aspect of the present invention.
Figure 8:
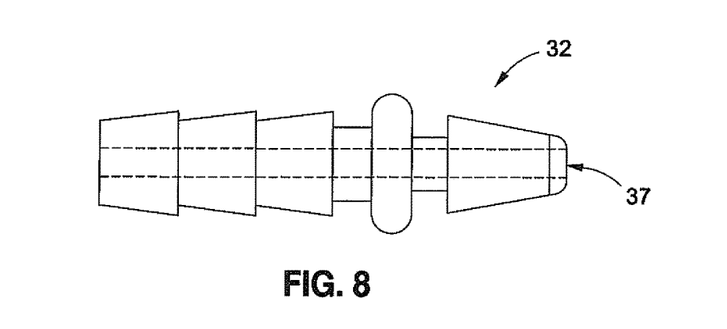
FIG. 8 is a side view of an inflation tip according to another aspect of the present invention.
Figure 9:
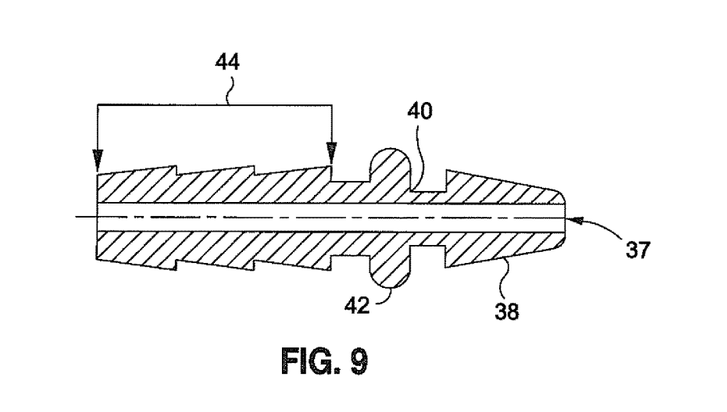
FIG. 9 is a cross-sectional view of the inflation tip of FIG. 8.

FIG. 7 depicts a filler tube 30. The filler tube is comprised of a long flexible tube 34 having a lumen therethrough, an injection tip 32, and a connector 35 for connecting the filler tube to a fluid supply (not shown). The flexible tube 34 may be provided with reference length markers 36 to provide medical personnel with a visual indication of the position of fill tube 30 inside the patient. As shown in FIGS. 8 and 9, the injection tip 32 has an orifice 37 extending therethrough that allows for fluid communication through the flexible tube 34, and the injection tip 32. One of the ends of the injection tip may be tapered into a wedge shape 38 having its smallest cross-section at the distal end of the injection tip 32. The wedge shape 38 assists in the insertion of the injection tip 32 into slit valve 10. Further, the injection tip may include a reduced diameter portion 40, and an insertion stop 42 for positively engaging the opening 16 of valve 10. The other end of the injection tip 32 is provided with barbs 44 to retain flexible tube 34 in fluid-tight engagement with the injection tip.

In use, the filler tube 30 is connected to the valve 10 by inserting the injection tip 32 into opening 16 of the valve 10. The injection tip 32, upon full insertion into the valve, extends to a point approximately even with a top surface of the second chamber 26. The substantial wedge shape 38 of the injection tip matches the orientation of the first chamber 18, and the narrow cross-sectional portion of the injection tip 32 is held firmly by the neck 19 of valve 10 to form a seal preventing the egress of fluid from the second chamber 26 into the first chamber 18 and out through the opening 16. The insertion stop 42 on the injection tip 32 prevents the injection tip from being inserted into the valve 10 beyond a pre-determined point. Upon full insertion, the insertion stop 42 rests against the flange 12 of valve 10. The opening 16 is of a size that, upon insertion of the injection tip 32, a second seal is formed by the interference of the flange 12 and the reduced diameter portion 40 of the injection tip. This second seal further insures that fluid does not exit the valve 10 and prevents other contaminants from entering the valve 10.

Figure 2:
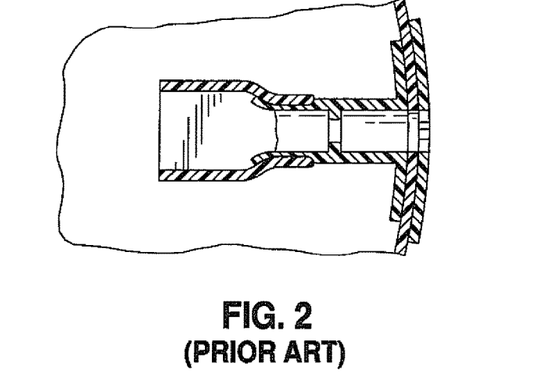
FIG. 2 is a cross-sectional view of a prior art one-way valve.

The valve 10 may be attached to an inflatable medical device such as a gastric balloon, a mammary implant, such as a Becker-style breast implant, a tissue expander, or the like. Other non-inflatable applications of the valve include devices such as a shunt drug delivery or therapeutic delivery system, a feeding tube, or the like. Accordingly, these variations are contemplated within the scope of the present invention. Where the device is a gastric balloon, the valve 10 is attached to the shell substantially as shown in Prior Art FIGS. 1 and 2. The flange surface 12 is placed flush with the exterior surface of the balloon and may be covered by an elastomeric sheath material that bonds the components together forming an integral gastric balloon and valve combination. The gastric balloon is inserted into a patient in a deflated state and inflated after insertion. Following insertion of the gastric balloon, a fluid, typically sterile saline, is injected into the gastric balloon via the filler tube 30. Other fluids, including air, silicone, pseudogel, oil, etc., may be used to fill an implant.

To inflate the gastric balloon, the valve 10 must have a slit 24. The slit 24 is preferably a single separation of two sides of the valve body 14. The slit 24 is formed during manufacturing by inserting a sharp thin tool (not shown) into the valve body 14. The length of the slit 24 is variable depending on the application of the valve and the desired opening pressure of the valve. In certain applications it may be necessary to insure that slit valve permits backflow more readily. In such instances, a shorter slit length would be used, whereas in instances where greater pressure must be contained by the valve, a longer slit length is desirable.

Referring to FIGS. 4, 7-9 and 11, to effectuate inflation of a balloon 50 via the filler tube 30, the injection tip 32 is inserted into the opening 16 of the flange 12 of the valve 10 placed in the wall of the balloon 50. The distal end of injection tip 32 extends to form a seal with neck 19. When pressurized fluid is injected through the filler tube 30 and orifice 37 of the injection tip 32, a higher pressure is created in the second chamber 26 having two effects. The first is to increase the sealing pressure of the neck 19 on the injection tip 32. The second effect is to force the slit 24 to open. The decreased wall thickness of the valve body 14 in the area of the second chamber 26 is more readily deformed by the pressurized fluid injected into the second chamber 26 than the area of the slit 24. The increased pressure causes the second chamber 26 to expand in a direction substantially perpendicular to the direction of the slit 24. This expansion in turn causes the slit 24 to be opened and permits the flow of fluid from the second chamber 26 through the slit 24 and into the implant. The opening of the slit is assisted by the concave surface 20. Similarly, if the second surface 22 is also concave, sufficient pressure may be applied to the shell to overcome the backflow resistance of the valve to permit the flow of fluid through the slit 24 to the exterior of the implant. Due to the relative sizes of the second chamber 26 and the concave surface 22, a far greater pressure is required to permit the backflow of fluid from the implant out of the valve than is required for inflation. For this reason the balloon or other implant may also be deflated or reduced in volume by inserting a small diameter probe or tube completely through the valve and into the interior of the implant shell. Concave surface 20 assists in guiding the small-diameter probe or tube into and through the valve body 14.

The valve 10 and the filler tip 32 when used in combination create a system that overcomes many of the shortcomings of the prior art. Through the use of the opening 16 and its interaction with the reduced diameter portion 40 of the injection tip 32, and also because of the interaction of the neck 19 with the injection tip 32, the injection tip is held firmly in place and is prevented from being forced out of the valve 10 during the injection of fluid through the valve 10. Further, because of these same features, withdrawal of the injection tip 32, when desired by the user, is greatly eased requiring less than 4 lb (17.8 N) of force to remove the tip from a balloon filled to 700 cm$^3$. Still further, the valve 10 provides for a device that does not leak under normal operating conditions yet still allows for two-way flow. The valve of the present invention allows continuous fluid flow at 30 psi (2.11 Kg/cm$^2$) and can safely withstand fluid fill pressures of up to 40 psi (2.81 Kg/cm$^2$) without damage to the valve.

Figure 10:
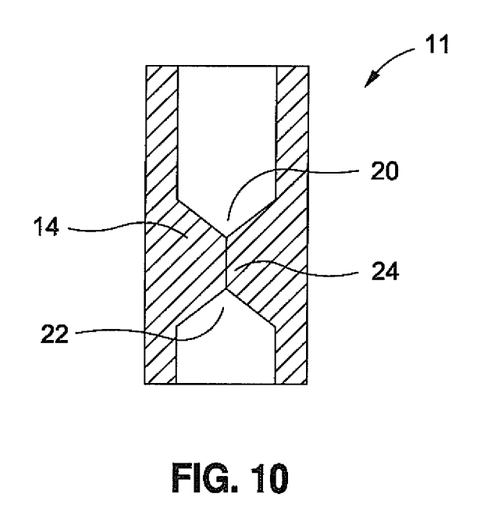
FIG. 10 is a cross-sectional view of a two-way valve according to another aspect of the present invention.
Figure 11:
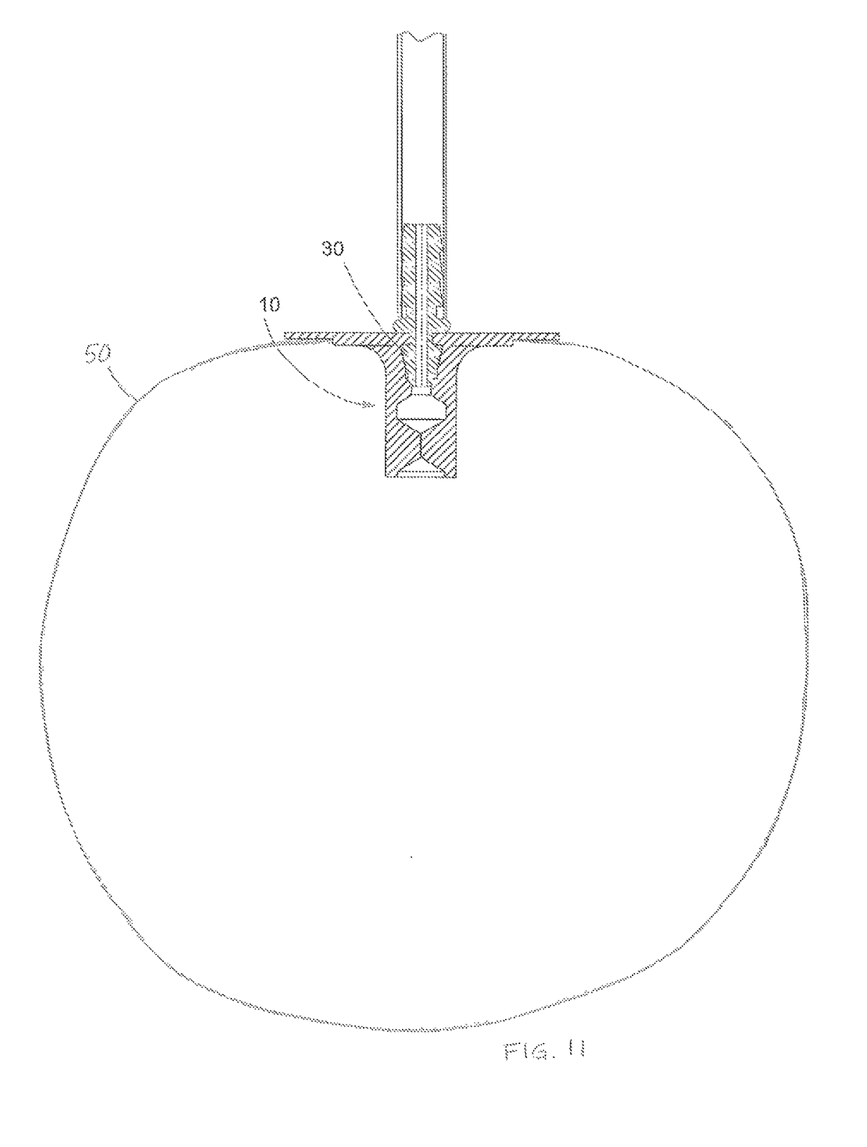
FIG. 11 is a cross-sectional view of a distal end of a filler tube inserted into a valve in a gastric balloon.

FIG. 10 depicts another aspect of the present invention. FIG. 10 shows a valve 11 having many of the features of the valve 10 shown in FIGS. 3-6. Valve 11 has a first concave surface 20, a second concave surface 22, and a slit 24, all housed in a body 14. The valve 11 operates in a similar fashion to valve 10. Upon application of a predetermined fluid pressure to one of either the first or second concave surfaces, 20 or 22, the slit 14 will open and allow fluid to pass. However, at pressures below the predetermined value, the slit valve insures that there is no fluid flow. The relative geometries of the concave surfaces 20, 22, the length of the slit 24, and the valve body 14 determine the opening pressure of the valve 11 and whether a greater pressure is required for flow in one direction compared to flow in the other direction. Such a valve would be useful in applications where the use of a flange 12, as shown in FIG. 3, is undesirable or unfeasible, for example in a feeding tube or a drug delivery shunt.

Although the invention has been particularly shown and described with reference to certain preferred embodiments, it will be readily appreciated by those of ordinary skill in the art that various changes and modifications may be made therein without departing from the spirit and scope of the invention.

We claim:

1. A method of preparing an inflatable medical implant for inflation, comprising:
providing an inflatable implant formed of a flexible polymer material suitable for residence in the body, the implant including a slit valve provided in a wall of the flexible polymer material comprising an elastomeric valve body defining proximal and distal ends, the proximal end of the valve body having a proximal opening therein, an open internal chamber formed within the valve body being in open fluid communication with the proximal opening, the internal chamber having a concave section at its distal end, and a normally closed slit formed in a portion of the valve body connecting the concave section of the internal chamber and the distal end of the valve body;

providing a filler tube having a lumen therethrough, the filler tube defining an injection tip having a distal end, the injection tip further including an insertion stop located proximal to the distal end of the injection tip; and inserting the filler tube through the proximal opening of the valve body until the injection tip positively engages a portion of the internal chamber to form a first fluid seal proximal to and spaced apart from the concave section; and wherein when fluid is introduced through the filler tube into the internal chamber at a threshold pressure differential across the slit, the slit is caused to open and permit fluid to pass distally therethrough into the inflatable implant;

wherein the proximal opening is surrounded by a flange, and the injection tip includes a reduced diameter portion located between the distal end of the injection tip and the insertion stop, the distal end of the injection tip comprises a tapered portion, the reduced diameter portion having an outer diameter smaller than an outer diameter of a distal end of the insertion stop and smaller than an outer diameter of a proximal end of the tapered portion, and wherein the insertion stop is sized to positively engage and form a seal with the proximal opening, and limit a distance to which the injection tip extends into the internal chamber, at which distance the distal end of the injection tip is sized to form the first fluid seal with a portion of the internal chamber and remains spaced proximally from the concave section, and at which distance a second seal is formed by an interference of the flange and the reduced diameter portion of the injection tip, wherein when the second seal is formed, the flange is retained between the insertion stop and the distal end of the injection tip and prevents the injection tip from separating from the slit valve when fluid pressure in the internal chamber is at the threshold fluid pressure differential across the slit.

2. The method of claim 1, wherein the filler tube is inserted through the proximal opening of the valve body until the insertion stop positively engages the valve body.

3. The method of claim 1, further comprising delivering the inflatable implant with the filler tube inserted in the valve body to a body cavity.

4. The method of claim 3, wherein the inflatable implant is a gastric balloon and the flexible polymer material is suitable for residence in the stomach, and wherein the step of delivering the inflatable implant includes passing it through the esophagus.

5. The method of claim 1, further comprising: before the step of introducing, delivering the inflatable implant with the filler tube engaged within the valve body to a body cavity.

6. The method of claim 5, wherein the body cavity is the stomach.

* * * * *